(12) United States Patent
Gelbin et al.

(10) Patent No.: US 8,049,041 B2
(45) Date of Patent: Nov. 1, 2011

(54) PHOSPHITE STABILIZER FOR LUBRICATING BASE STOCKS AND THERMOPLASTIC POLYMERS

(75) Inventors: Michael E. Gelbin, Middlebury, CT (US); Jun Dong, Cheshire, CT (US)

(73) Assignee: Chemtura Corporation, Middlebury, CT (US)

( * ) Notice: Subject to any disclaimer, the term of this patent is extended or adjusted under 35 U.S.C. 154(b) by 375 days.

(21) Appl. No.: 12/163,557

(22) Filed: Jun. 27, 2008

(65) Prior Publication Data

US 2010/0016196 A1    Jan. 21, 2010

(51) Int. Cl.
*C07F 9/6574*    (2006.01)
(52) U.S. Cl. .......................................... 568/12
(58) Field of Classification Search .................. None
See application file for complete search history.

(56) References Cited

U.S. PATENT DOCUMENTS

| | | | |
|---|---|---|---|
| 2,612,488 A | 9/1952 | Nelson | |
| 3,556,999 A | 1/1971 | Messina et al. | |
| 3,652,411 A | 3/1972 | Commichau | |
| 3,923,672 A | 12/1975 | Durr, Jr. et al. | |
| 4,652,385 A | 3/1987 | Cohen | |
| 5,124,057 A | 6/1992 | Cohen | |
| 5,232,614 A | 8/1993 | Colclough et al. | |
| 5,688,847 A | 11/1997 | Gelbin et al. | |
| 6,172,014 B1 | 1/2001 | Meyers | |
| 6,326,336 B1 | 12/2001 | Gatto | |
| 2003/0171227 A1 | 9/2003 | Holt et al. | |
| 2004/0236133 A1* | 11/2004 | Selent et al. | 558/153 |
| 2006/0069000 A1 | 3/2006 | Dong et al. | |
| 2006/0073992 A1 | 4/2006 | Dong et al. | |
| 2006/0223918 A1 | 10/2006 | Gelbin et al. | |

FOREIGN PATENT DOCUMENTS

| | | | |
|---|---|---|---|
| EP | 0316610 A1 | | 5/1989 |
| JP | 06-025493 | * | 2/1994 |
| WO | 2007149143 A2 | | 12/2007 |

OTHER PUBLICATIONS

Konovalova et al. Russian Journal of General Chemistry. vol. 72, No. 8, 2002.*
Machine translation of JP 06-025493, Accessed from aipn website on Jul. 18, 2011.*

* cited by examiner

*Primary Examiner* — Rebecca Anderson
*Assistant Examiner* — Alicia L Otton
(74) *Attorney, Agent, or Firm* — Joseph Suhadolnik

(57) ABSTRACT

A substituted phosphite suitable for lubricating base stocks and thermoplastic polymers represented by the structure:

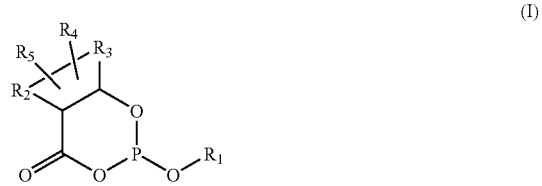

(I)

wherein $R_1$ is selected from the group consisting of $C_1$-$C_{22}$ alkyl and $C_4$-$C_{22}$ cycloalkyl; $R_2$ and $R_3$ are selected to form a $C_5$-$C_{18}$ aryl; and $R_4$ and $R_5$ are selected from the group consisting of H, $C_1$-$C_{22}$ alkyl, $C_2$-$C_{22}$ alkenyl, $C_4$-$C_{22}$ cycloalkyl, and $C_5$-$C_8$ aryl. The substituted phosphite may be combined with at least one primary antioxidant as well as other additives.

3 Claims, No Drawings

PHOSPHITE STABILIZER FOR LUBRICATING BASE STOCKS AND THERMOPLASTIC POLYMERS

BACKGROUND OF THE INVENTION

1. Field of the Invention

The present invention relates to novel liquid phosphite compositions useful as antioxidants for thermoplastic polymers and lubricant additives compositions. The present invention relates to phosphite stabilizer compositions, and in particular additive blends comprising a phosphite stabilizer for lubrication compositions and solid compositions of thermoplastic polymers.

2. Discussion of the Background Information

There is a continuing demand for liquid phosphite stabilizers for lubricant, thermoplastics and elastomer applications. Plastics, elastomers and lubricants when exposed to heat and oxygen (air), which are ubiquitously present during their manufacture, transportation, storage, or use, will undergo oxidation. Oxidation can cause deterioration of materials properties (discoloration, embrittlement, softening) to the extent of catastrophic failure. Lubricants, for example, oxidize to form undesirable oxidation by-products that contribute to an increase in total acidity, formation of gums, discoloration, polymerization, rancidity, and/or odor. As a consequence, loss of designated physical and tribological properties of the oils may occur. Conventional antioxidants, including aromatic secondary aminic antioxidants and phenolic antioxidants, are effective, at least to some extent, in controlling the oxidation of lubricating oils and are being widely used. The performances of the conventional antioxidants are generally satisfactory when the lubricants to be protected are used under relatively mild conditions without prolonged exposure to elevated temperatures and contaminants. It is known that in more extreme service environments, especially those contaminated with catalytic transition metals, such as iron, the decomposition rates of lubricants may increase so dramatically that even at higher concentrations, such conventional aminic and phenolic antioxidants do not retard oxidation effectively.

Industrial turbines, such as those commonly used for power generation, require the use of high quality lubricants. Conventional lubricants, such as the original rust and oxidation ("R&O") type circulating oils that are based on API Group I/II/III base oils and conventional additives, have a long and successful history of application for use in many turbine systems, for example, hydraulic systems. However, with the evolution of new turbine equipment that operates under more severe conditions of thermal and mechanical stress, it is necessary to use suitable turbine lubricants having carefully balanced additive packages and compatible base stocks for optimum oxidative stability and anti-wear properties.

An effective method to address the aforementioned issue of iron-catalyzed oil oxidation is the use of metal deactivators that can counteract the catalytic effects from iron and other transition metals. However, as stated in the EP Publication No. 0 316 610 A1, the addition of metal deactivators to lubricants has given rise to a problem of decreasing the critical anti-seizure and antiwear properties of the antiwear/extreme pressure agents that are commonly used in lubricant formulations.

Lubricant compositions containing aromatic secondary amines and substituted phenols are widely known in the art. Likewise, turbine lubricants containing various alkylated diphenylamines and hindered phenols as primary antioxidants are known, such as U.S. Pat. No. 6,326,336 which uses an antioxidant comprising an alkylated diphenylamine and/or phenylnaphthylamines, and sulfurized olefins and/or sulfurized fatty acids and/or ashless dithiocarbamates and/or tetraalkylthiuram disulfides.

The use of secondary antioxidants, such as organophosphites, as stabilizers for various lubricating substances is also known. These lubricant compositions include an organophosphite and a substituted phenol or aromatic secondary amine are also known.

U.S. Pat. No. 3,556,999 discloses hydraulic fluid compositions, particularly automatic transmission fluid compositions, containing a major amount of lubricating oil and a minor amount of each of (A) a phosphite or disubstituted phosphate, (B) a substituted phenol or an aromatic secondary amine and (C) an oil-soluble dispersant copolymer containing N-vinyl-2-pyrrolidone.

U.S. Pat. No. 3,652,411 discloses a polyglycol base lubricant containing, in minor proportion, as a stabilizer, a mixture comprising: a substituted amine, an aliphatically substituted phenol, and organic phosphate, a polyhydroxyquinone, a benzotriazole, an amine salt and a substituted organic phosphite.

U.S. Pat. No. 3,923,672 discloses a lubricating oil composition said to be particularly suitable for use in steam turbines or gas turbines. The turbine oil composition comprises a major amount of a mineral or synthetic hydrocarbon base oil and an effective amount of a combination of the following materials: triphenyl phosphite or a trialkyl-substituted phenyl phosphite; diphenylamine or alkylated diphenylamine; phenyl α-naphthylamine, phenyl β-naphthylamine, alkyl or alkylaryl substituted phenyl α-naphthylamine, or alkyl or alkaryl substituted phenyl β-naphthylamine; benzotriazole or alkyl-substituted benzotriazole; partial ester of alkyl or alkenyl succinic anhydride. In a preferred aspect, the turbine oil composition contains additionally an effective amount of a copolymer of N-vinyl-2-pyrrolidone and an α-olefin.

U.S. Pat. No. 4,652,385 discloses lubricant compositions of a low-volatility tri-substituted phosphite and low-volatility sterically hindered phenolic stabilizers that provide effective antioxidant qualities to lubricating oils selected from hydrotreated oils, poly-alpha-olefin oils and paraffinic white oils, and mixtures thereof.

U.S. Pat. No. 5,124,057 discloses lubricant compositions of a low-volatility tri-substituted phosphite and selected substituted isocyanurate phenolic stabilizers that provide antioxidant qualities to lubricating oils selected from hydrotreated oils, poly-alpha-olefin oils, paraffinic white oils and mixtures thereof.

U.S. Pat. No. 5,232,614 discloses that substituted para-phenylene diamines have been found to be effective antioxidants capable of protecting crankcase lubricating oils from thickening and sludge formation after prolonged exposure to oxygen at elevated temperature. Additional anti-wear additives such as di- and tri-alkyl, cycloalkyl and aryl phosphites are also disclosed.

U.S. Pat. No. 5,688,847 discloses a fluorophosphite compound of the formula:

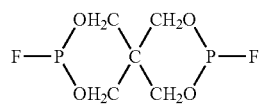

This compound shows superior performance as a stabilizer in polymers, such as polypropylene, and polyvinyl chloride. Also disclosed is a process for making this compound.

U.S. Pat. No. 6,172,014 discloses an improved method of reducing compressor gas leakage by providing a compression cylinder with a lubricant comprising less than about 1% of a synergistic mixture of antioxidants, wherein the antioxidant mixture comprises at least one phosphite antioxidant and at least one other antioxidant.

U.S. Publication No. 2003/0171227 discloses stabilizing compositions for lubricant base stocks and lubricant formulations that are composed of a mixture of (a) at least one aromatic aminic amine antioxidant optionally blended with at least one hindered phenolic antioxidant and (b) at least one neutral organo phosphate or phosphite, optionally blended with at least one acid organo phosphate or phosphite.

U.S. Publication Nos. 2006/0073992 and 2006/0069000 disclose a stabilized lubricant composition that comprises lubricating oil and a mixture of (a) at least one organophosphite compound and (b) at least one aromatic secondary amine or one substituted phenol or mixtures thereof. The compositions have been found to be highly resistant to oxidation under demanding service conditions and to be useful as turbine lubricants.

U.S. Publication No. 2006/0223918 discloses compounds of the structure:

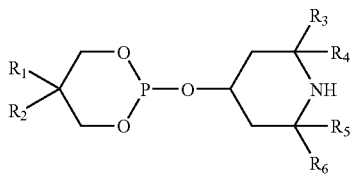

wherein $R_1$, $R_2$, $R_3$, $R_4$, $R_5$, and $R_6$ are independently selected alkyl groups, provided that $R_1$ is different from $R_2$. The compounds are useful as stabilizers for thermoplastic resins.

International Publication No. WO2007/149143 discloses a compound comprises a blend of at least two different phosphites of the structure

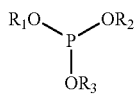

wherein $R_1$, $R_2$, and $R_3$ are independently selected alkylated aryl groups and wherein said blend is a liquid at ambient conditions. The compositions are useful for stabilizing thermoplastic resins and elastomers.

The disclosures of the foregoing are incorporated herein by reference in their entirety.

SUMMARY OF THE INVENTION

There is a continuing demand for liquid phosphite stabilizers for lubrication base stocks and thermoplastic elastomer applications. In a first aspect of the present invention, there is provided a composition of matter comprising a compound of the structure:

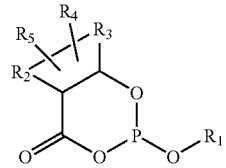

(I)

wherein $R_1$ is selected from the group consisting of $C_1$-$C_{22}$ alkyl and $C_4$-$C_7$ cycloalkyl; $R_2$ and $R_3$ are selected to form a $C_5$-$C_{18}$ aryl; and $R_4$ and $R_5$ selected from the group consisting of H, $C_1$-$C_{22}$ alkyl, $C_2$-$C_{22}$ alkenyl, $C_4$-$C_{22}$ cycloalkyl, and $C_5$-$C_8$ aryl. In one embodiment, if $R_5$ is H then $R_4$ is selected from the consisting of $C_1$-$C_{22}$ alkyl, $C_2$-$C_{22}$ alkenyl, $C_4$-$C_{22}$ cycloalkyl, and $C_5$-$C_8$ aryl. Optionally, the alkyl and alkenyl groups may be branched and/or the cycloaklyl and aryl groups may be substituted. In a preferred embodiment, $R_1$ and $R_4$ are each independently selected from the group consisting of 2-ethyl-hexyl, n-octyl, and iso-octyl.

In a second aspect of the present invention, there is provided a method for making a compound having the structure

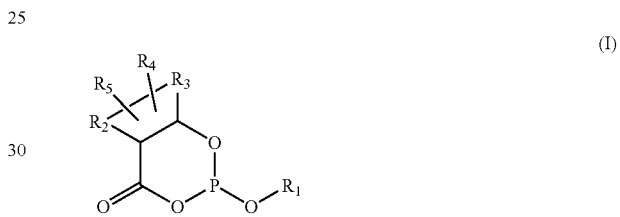

(I)

wherein $R_1$ is selected from the group consisting of $C_1$-$C_{22}$ alkyl and $C_4$-$C_{22}$ cycloalkyl; $R_2$ and $R_3$ are selected to form a $C_5$-$C_{18}$ aryl; and $R_4$ and $R_5$ are selected from the group consisting of H, $C_1$-$C_{22}$ alkyl, $C_2$-$C_{22}$ alkenyl, $C_4$-$C_{22}$ cycloalkyl, and $C_5$-$C_8$ aryl, the method comprising: a) reacting a phosphorus trihalogen compound with a beta hydroxy acid compound to form a halogenphosphonite intermediate; and b) reacting the halogenphosphonite intermediate of step a) with an alcohol to form the compound.

In a third aspect of the present invention, there is provided a method for forming a lubricating composition comprising: blending at least one primary antioxidant selected from the group consisting of secondary diarylamines, substituted phenols, and a blend thereof, and a substituted phosphite compound of the structure:

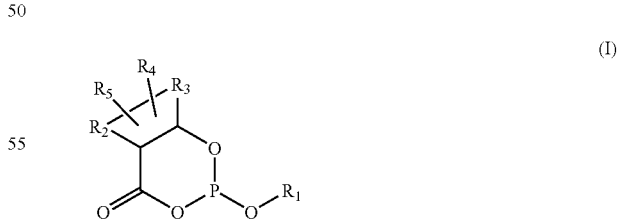

(I)

wherein $R_1$ is selected from the group consisting of $C_1$-$C_{22}$ alkyl and $C_4$-$C_{22}$ cycloalkyl; $R_2$ and $R_3$ are selected to form a $C_5$-$C_{18}$ aryl; and $R_4$ and $R_5$ are selected from the group consisting of H, $C_1$-$C_{22}$ alkyl, $C_2$-$C_{22}$ alkenyl, $C_4$-$C_{22}$ cycloalkyl, and $C_5$-$C_8$ aryl, to form an additive blend; an adding the additive blend to a lubricating base stock.

In a fourth aspect of the present invention, there is provided a lubricating composition comprising: a) a lubricating base stock; and b) an additive blend comprising: i) at least one primary antioxidant; and ii) a substituted phosphite compound represented by the following general formula:

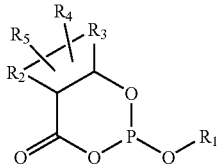

(I)

wherein $R_1$ is selected from the group consisting of $C_1$-$C_{22}$ alkyl and $C_4$-$C_{22}$ cycloalkyl; $R_2$ and $R_3$ are selected to form a $C_5$-$C_{18}$ aryl; and $R_4$ and $R_5$ are selected from the group consisting of $C_1$-$C_{22}$ alkyl, $C_2$-$C_{22}$ alkenyl, $C_4$-$C_{22}$ cycloalkyl, and $C_5$-$C_8$ aryl. In one embodiment, the weight percent (wt %) of substituted phosphite compound based on the total mass of the composition is from 0.01 to 5 wt. %, e.g. from 0.1 to 1.5 wt %. The primary antioxidant may be from 0.01 to 5 wt. %, e.g. from 0.1 to 1.5 wt % based on the total mass of the composition. Optionally, the lubricating composition may also one or more additives, such as viscosity index improvers, corrosion inhibitors, dispersants, lube oil flow improvers, detergents/rust inhibitors, pour point depressants, antifoamants, antiwear agents, seal swell agents, friction modifiers, and metal deactivators.

In a fifth aspect of the present invention, there is provided a solid composition comprising: a thermoplastic elastomer; and substituted phosphite compound of the structure:

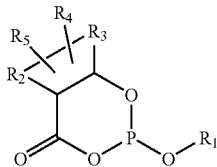

(I)

wherein $R_1$ is selected from the group consisting of $C_1$-$C_{22}$ alkyl and $C_4$-$C_{22}$ cycloalkyl; $R_2$ and $R_3$ are selected to form a $C_5$-$C_{18}$ aryl; and $R_4$ and $R_5$ are selected from the group consisting of H, $C_1$-$C_{22}$ alkyl, $C_2$-$C_{22}$ alkenyl, $C_4$-$C_{22}$ cycloalkyl, and $C_5$-$C_8$ aryl. In one embodiment, the thermoplastic elastomer comprises polyethylene, polypropylene, polypropylene, polyisobutylene, polybutene-1, polymethylpentene-1, polyisoprene, or polybutadiene.

DETAILED DESCRIPTION OF THE PREFERRED EMBODIMENTS

This invention relates to stabilized compositions comprising a lubricating base stock or thermoplastic elastomer and an additive blend of the substituted phosphite compound and primary antioxidants. Such substituted phosphite compounds and additive blends impart excellent anti-oxidative stabilities and are particularly suitable for use in a high temperature iron-catalyzed environment. The substituted phosphite compound of the present invention, which acts as a secondary antioxidant, also known as a hydroperoxide decomposer, is represented by the following general formula:

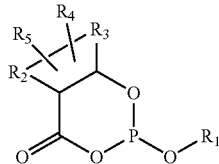

(I)

wherein $R_1$ is selected from the group consisting of straight or branched $C_1$-$C_{22}$ alkyl and substituted or unsubstituted $C_4$-$C_{22}$ cycloalkyl; $R_2$ and $R_3$ are selected to form a $C_5$-$C_{18}$ aryl; and $R_4$ and $R_5$ are selected from the group consisting of hydrogen straight or branched $C_1$-$C_{22}$ alkyl, straight or branched $C_2$-$C_{22}$ alkenyl, substituted or unsubstituted $C_4$-$C_{22}$ cycloalkyl, and substituted or unsubstituted $C_5$-$C_8$ aryl.

If one or more of the $R_1$, $R_4$ and $R_5$ groups are cycloalkyl or aryl groups, the cycloalkyl and aryl may be substituted with a linear or branched $C_1$-$C_{12}$ alkyl group.

In one embodiment, the present invention comprises a substituted phosphite compound where $R_1$, $R_4$ and $R_5$ have the same number of carbon atoms. In one embodiment, $R_5$ is preferable hydrogen and $R_4$ is not hydrogen.

Representative examples of alkyl groups for use herein with one or more of $R_1$, $R_4$, $R_5$ and alkyl groups used throughout this application include, for example, a straight or branched hydrocarbon chain radical containing from 1 to 22 carbon atoms, e.g., n-propyl, 1-methylethyl (isopropyl), n-butyl, isobutyl, 2,2,3,3-tetramethylbutyl, n-pentyl, 1,3-dimethylpentyl, 3-ethyl-2-methylpentyl, 3-ethyl-3-methylpentyl, 2,3,3-trimethylpentyl, 2,2-dimethylhexyl, 2,3,4-trimethylpentyl, n-hexyl, 1,4-dimethylhexyl, 2,3-dimethylhexyl, 2,5-dimethylhexyl, 2-ethyl-hexyl, 3-ethyl-hexyl, n-heptyl, 2-methylheptyl, 3-methylheptyl, 4-methylheptyl, 1,5-dimethylheptyl, n-octyl, octyl, iso-octyl, nonyl, decyl, etc., mixtures and isomers thereof, and the like.

In one embodiment, $R_1$ is a straight or branched $C_4$-$C_{10}$ alkyl group and preferably is a straight or branched $C_8$ alkyl. Such preferred $C_8$ alkyl groups include 2-ethyl-hexyl, n-octyl, and iso-octyl.

Representative examples of cycloalkyl groups for use herein with one or more of $R_1$, $R_4$, $R_5$ and cycloalkyl groups used throughout this application include, for example, substituted or unsubstituted rings containing from 4 to 22 carbon atoms, e.g., cyclopentyl, n-ethyl-cyclopentyl, n-propyl-cyclopentyl, n-di-methyl-n-ethylpentyl, n-trimethylpentyl, cyclohexyl, n-methyl-cyclohexyl, n-dimethyl-cyclohexyl, n-ethyl-cyclohexyl, cycloheptyl, n-methyl-cycloheptyl, cyclooctyl, n-methyl-cyclooctyl, etc., mixtures and thereof, and the like.

Representative examples of aryl groups for use herein with one or more of the combined aromatic ring of $R_2$ and $R_3$, $R_4$, $R_5$, and aryl groups used throughout this application include, for example, substituted or unsubstituted aromatic rings containing from 5 to 18 carbon atoms, e.g., phenyl, n-methylphenyl, n-dimethylphenyl, n-ethylphenyl, benzyl, naphthyl, tetrahydronapthyl, indenyl, biphenyl, etc., mixtures and isomers thereof, and the like.

Optionally, the cycloalkyl or aryl groups of the present invention may also be substituted with one or more of the groups selected from the group consisting of halogen, hydroxyl, carbonyl, mercapto, nitro, nitroso, sulfoxy, cyano, etc. Further, the cylcoalkyl or aryl groups may comprise one or more heteroatoms such as N, S, or O.

Representative examples of alkenyl groups for use herein with one or more of $R_4$, $R_5$ and alkenyl groups used throughout this application include, for example, a straight or branched hydrocarbon chain radical containing from 2 to 22 carbon atoms, e.g., propenyl, n-butenyl, isobutenyl, pentenyl, hexenyl, n-heptenyl, octenyl, iso-octenyl, nonenyl, decenyl, etc., mixtures and isomers thereof, and the like.

As indicated above, when $R_2$ and $R_3$ are connected to form a $C_6$ aryl, i.e. phenyl, the substituted phosphite compound may be represented by the structure:

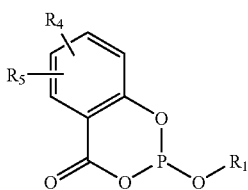

(II)

wherein $R_1$, $R_4$ and $R_5$ are defined above.

An exemplary substituted phosphite of the present invention includes a 4-oxo-1,3-dioxa-2-phosphanaphthalene compound represented by the structure:

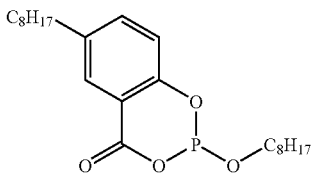

(III)

wherein each $C_8H_{17}$ may independently be a straight or branched alkyl group.

Another exemplary substituted phosphite of the present invention includes a 4-oxo-1,3-dioxa-2-phosphanaphthalene compound represented by the structure:

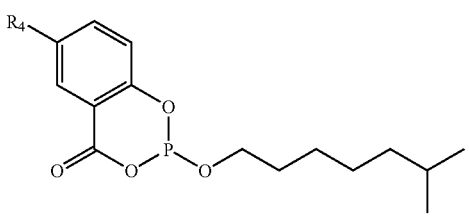

(IV)

wherein $R_4$ is defined above and $R_5$ is hydrogen.

In accordance with one embodiment of the present invention, there is provided a method for making substituted phosphites of the present invention that involves reacting a beta hydroxy acid (BHA) with a phosphorus trihalogen, following by reacting an alcohol. Suitable BHAs include those represented by the structure:

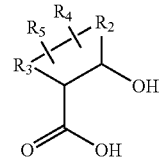

(V)

wherein $R_2$, $R_3$, $R_4$ and $R_5$ are defined above. An exemplary beta hydroxy acid includes alkylated salicylic acid, such as 4-octyl-salicyclic acid. Suitable phosphorus trihalogen include phosphorus trichloride, phosphorus trifluoride, and phosphorus tribromide. Suitable alcohols include $C_1$-$C_{22}$ alcohols including, but not limited to, 2-ethyl-hexanol, n-octanol, octanol, and iso-octanol.

The reaction of BHA and phosphorus trihalogen is carried out in a nitrogen or similarly inert atmosphere at normal atmospheric pressure. In addition, this reaction may be carried out in the presence of a tertiary amine, such as an triethyl amine or pyridine, and a solvent, such as toluene, cumene, benzene, chlorobenzene, xylene, heptane, hexane, etc. The pot temperature is maintained at a temperature of from $-15°$ C. to $15°$ C., e.g. $-10°$ C. to $10°$ C. or $0°$ C. to $5°$ C. This reaction forms a halogenated intermediate.

The halogenated intermediate is further reacted with the alcohol, under the same conditions as the first step. The reaction product is filtered, using a vacuum filter, to produce the substituted phosphites of the present invention.

In one embodiment there is provided a composition comprising an additive blend of the substituted phosphite described above in formulas I-IV. Additive blends of the present invention may also include at least one primary antioxidant. The primary antioxidants, also known as free radical scavenging antioxidants, suitable for use with additive blends of the present invention include aminic compounds, phenolic compounds, and mixtures thereof.

In one embodiment there is provided a composition comprising an additive blend of the substituted phosphite described above in formulas I-IV and at least one aminic compound. Suitable aminic compounds include those described in U.S. Ser. No. 11/128,929, the entire contents and disclosure of which are incorporated by reference. One such suitable aminic compound may be represented by the structure:

$R_6$—NH—$R_7$ wherein $R_6$ and $R_7$ are independently hydrocarbyl groups having 6 to 100 carbon atoms, such as alkyl, alkenyl, aryl, cycloalkyl, or combinations thereof.

In a further embodiment, a suitable aminic compound may be a secondary diarylamine compound represented by the following general formula:

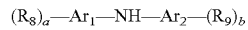

$(R_8)_a$—$Ar_1$—NH—$Ar_2$—$(R_9)_b$ wherein $Ar_1$ and $Ar_2$ are independently aromatic hydrocarbon groups and $R_8$ and $R_9$ are independently hydrogen or alkyl, alkenyl, cycloalkyl, or aryl groups having from 6 to about 100 carbon atoms and a and b are independently 0 to 3 but (a+b) is not greater than 4.

Examples of some of the secondary diarylamine compounds that are useful in the practice of the present invention include, but are not limited to, diphenylamine, monoalkylated diphenylamine, dialkylated diphenylamine, trialkylated diphenylamine, or mixtures thereof, 3-hydroxydiphenylamine, 4-hydroxydiphenylamine, mono- and/or di-butyl-diphenylamine, mono- and/or di-octyldiphenylamine, monoand/or di-nonyldiphenylamine, phenyl-α-naphthylamine, phenyl-β-naphthylamine, diheptyldiphenylamine, mono- and/or di-(α-methylstyryl) diphenylamine, mono- and/or distyryidiphenylamine, 4-(p-toluenesulfonamido)diphenylamine, 4-isopropoxydiphenylamine, t-octylated N-phenyl-1-naphthylamine, mixtures of mono- and dialkylated t-butyl-t-octyldiphenylamines, N-phenyl-1,2-phenylenediamine, N-phenyl-1,4-phenylenediamine, N,N'-diphenyl-p-phenylenediamine, N,N'-di(naphthyl-2-)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, and N-cyclohexyl-N'-phenyl-p-phenylenediamine. The following are exemplary of the secondary diarylamine compounds just defined and are commercially available from Chemtura Corporation: Naugalube™ 438, Naugalube 438L, Naugalube 640, Naugalube 635, Naugalube 680, Naugalube AMS, Naugalube APAN, Naugard PANA, Naugalube 403, Naugalube 410, and Naugalube 420;from Ciba-Geigy: Irganox™ L 06 and Irganox L 57;from R.T. Vanderbilt: Vanlube SL, Vanlube 961, Vanlube 81, Vanlube SS, Vanlube DND; and from Albermarle: Ethanox 4720, Ethanox 4793, Ethanox 4780.

In one embodiment there is provided a composition comprising an additive blend of the substituted phosphite described above in formulas I-IV and at least one phenolic compound. Suitable phenolic compounds include those described in U.S. Ser. No. 11/128,929, the entire contents and disclosure of which are incorporated by reference. One such phenolic compound includes a substituted phenol compound represented by the following general formula:

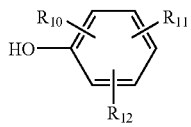

wherein $R_{10}$, $R_{11}$, and $R_{12}$ are independently hydrogen or hydrocarbyl groups having 1 to 100 carbon atoms, such as alkyl, alkenyl, aryl, or cycloalkyl, with the provision that at least one of the ortho position groups contain an alkyl chain. Preferably, the ortho alkyl chain comprises a branched alkyl chain having an iso- or tert-structure.

With wide variation in the composition of the hydrocarbyl groups, the substituted phenol compounds suitable for the invention may include alkylated mono-phenols; alkylated hydroquinones; hydroxylated thiodiphenyl ethers; alkylidenebisphenols; acylaminophenols; esters of (β-)3,5-di-tert-4-hydroxybenzene propionic acid with mono- or polyhydric alcohols; esters of (β-)5-tert-butyl-4-hydroxy-3-methylbenzene propionic acid with mono- or polyhydric alcohols; amides of beta(3,5di-tert-butyl-4-hydroxyphenyl) propionic acid. Examples of some of the phenolic antioxidants that are useful for the practice of this invention are 2,6-di-tert-butyl-4-methylphenol, 2,6-di-tert-butylphenol, 2-tert-butyl-4,6-dimethylphenol, 2,6-di-tertbutyl-4-ethylphenol, 2,6-di-tert-butyl-4-isobutylphenol, 2,6-bis(alphamethylbenzyl)-4-methylphenol and 2-alpha-methylbenzyl-4-methylphenol, and the like; 2,6-di-tert-butyl-4-methoxyphenol, 2,5-di-tert-butyl-hydroquinone and the like; 3,5-di-tert-butyl-4-hydroxybenzene-3-propionic acid esterified with methanol, octanol, octadecanol, 1,6-hexanediol, neopentyl glycol, thiodiethylene glycol, diethylene glycol, triethylene glycol, pentaerythritol, and the like. The following are exemplary of more preferred substituted phenol compounds that are commercially available from Chemtura Corporation: Naugard 431, Naugalube 531, Naugalube 38, Naugalube 15, and Naugalube 18;from Ciba-Geigy: Irganox™ L 115, Irganox L 118, Irganox L 135, and Irgalube F 10A; and from Albemarle: Ethanox 4712, Ethanox 4733, Ethanox 4735, Ethanox 4702.

Returning to the additive blends of the present invention, the additive blend will usually have a weight percent (wt %) of the substituted phosphite of the present invention based on the total weight of the additive blend of up to about 99 wt %, e.g., up to about 95 wt %, up to about 90 wt %, up to about 85 wt %, up to about 80 wt %, up to about 75 wt %, up to about 70 wt %, up to about 65 wt %, up to about 60 wt %, up to about 55 wt %, up to about 50 wt %, up to about 45 wt %, up to about 40 wt %, up to about 35 wt %, up to about 30 wt %, up to about 25 wt %, up to about 20 wt %, up to about 15 wt %, or up to about 10 wt %. In terms of ranges, the additive blend may comprise from 5 to 99 weight percent (wt %) based on the total weight of the additive blend, e.g. 15 to 80 wt %, 25 to 75 wt %, 20 to 60 wt % or 25 to 50 wt%, of the substituted phosphite. The additive blend may also comprise a primary antioxidant in an amount of 5 to 99 wt % based on the total weight of the additive blend, e.g. 15 to 80 wt %, 25 to 75 wt %, 20 to 60 wt % or 25 to 50 wt %. When a mixture of two primary antioxidants are used, the ratio between the primary antioxidants may be from 80:20 to 20:80 parts by weight, e.g. 60:40 to 40:60 or 50:50. In one such embodiment, the additive blend may comprise from 5 to 50 wt % based on the total weight of the additive blend of the substituted phosphite, 5 to 50 wt % of the secondary diarylamine, and 5 to 50 wt % of the substituted phenol.

In one embodiment there is a composition comprising the additive blend combined with a lubricating base stock. In general the composition may comprise from about 35 to 99.99 wt % based on the total weight of the composition, e.g. 85 to 99.5 wt % or 90 to 99 wt %, of lubricating base stock. The composition may also comprise from 0.01 to about 65 wt % based on the total weight of the composition, e.g. 0.5 to 15 wt % or 1 to 10 wt %, of the additive blend. In such embodiments, the substituted phosphite may be in an amount of 0.01 to 5 wt % based on the total weight of the composition, e.g. 0.05 to 2 wt % or 0.01 to 1.5 wt %. In such embodiments, the secondary diarylamine compound, when present, may be in an amount of 0.01 to 5 wt % based on the total weight of the composition, e.g. 0.05 to 2 wt % or 0.01 to 1.5 wt %. In such embodiments, the substituted phenol compound, when present, may be in an amount of 0.01 to 5 wt % based on the total weight of the composition, e.g. 0.05 to 2 wt % or 0.01 to 1.5 wt %.

An additive blend with one antioxidant consisting essentially of the substituted phosphite compound of the present invention may have an oxidation stability, as measured by a pressurized differential scanning calorimeter (PDSC) test @185° C., of from 20-300 minutes, e.g. from 30-150 minutes or from 35-100 minutes. An additive blend with two antioxidants consisting essentially of an aminic antioxidant and the substituted phosphite compound of the present invention may have an oxidation stability, as measured by the PDSC test @185° C., of from 250-400 minutes, e.g. from 260-350 minutes or from 270-325 minutes. An additive blend with two antioxidants consisting essentially of a phenolic antioxidant and the substituted phosphite compound of the present invention may have an oxidation stability, as measured by the PDSC test @185° C., of from 45-100 minutes, e.g. from 48-75 minutes or from 48-60 minutes. An additive blend with three antioxidants comprising of an aminic, a phenolic antioxidant and the substituted phosphite compound of the present invention, as measured by the PDSC test @185° C., of from 90-150 minutes, e.g. from 100-125 minutes or from 105-120 minutes. Optionally, the additive blend with three antioxidants do not comprise a dilauryl phosphite.

The additive blends of the present invention are especially useful as components in many different lubricating oil compositions. The additive blends can be included in a variety of oils with lubricating viscosity, including natural and synthetic lubricating oils and mixtures thereof. The additive blends can be included in crankcase lubricating oils for spark-ignited and compression-ignited internal combustion engines. The compositions can also be used in gas engine lubricants, steam and gas turbine lubricants, automatic transmission fluids, gear lubricants, compressor lubricants, metal-working lubricants, hydraulic fluids, and other lubricating oil and grease compositions.

In general, the lubricating oil base stock is any natural or synthetic lubricating oil base stock fraction having a kinematic viscosity at 100° C. of about 2 to about 200 centistokes (cSt), e.g. about 3 to about 150 cSt, or about 3 to about 100 cSt. The lubricating oil base stock can be derived from natural lubricating oils, synthetic lubricating oils, or mixtures thereof. Suitable lubricating oil base stocks include base stocks obtained by isomerization of synthetic wax and wax, as well as hydrocracked base stocks produced by hydrocracking (rather than solvent extracting) the aromatic and polar components of the crude. Natural lubricating oils include animal oils, such as lard oil, tallow oil, vegetable oils (e.g., canola oils, castor oils, sunflower oils), petroleum oils, mineral oils, and oils derived from coal or shale.

Synthetic oils include hydrocarbon oils and halo-substituted hydrocarbon oils, such as polymerized and interpolymerized olefins, gas-to-liquids prepared by Fischer-Tropsch technology, alkylbenzenes, polyphenyls, alkylated diphenyl ethers, alkylated diphenyl sulfides, as well as their derivatives, analogs, homologs, and the like. Synthetic lubricating oils also include alkylene oxide polymers, interpolymers, copolymers, and derivatives thereof, wherein the terminal hydroxyl groups have been modified by esterification, etherification, etc.

Another suitable class of synthetic lubricating oils comprises the esters of dicarboxylic acids with a variety of alcohols. Esters useful as synthetic oils also include those made from $C_5$ to $C_{18}$ monocarboxylic acids and polyols and polyol ethers. Other esters useful as synthetic oils include those made from copolymers of α-olefins and dicarboxylic acids which are esterified with short or medium chain length alcohols.

Silicon-based oils, such as the polyalkyl-, polyaryl-, polyalkoxy-, or polyaryloxy-siloxane oils and silicate oils, comprise another useful class of synthetic lubricating oils. Other synthetic lubricating oils include liquid esters of phosphorus-containing acids, polymeric tetrahydrofurans, poly-α-olefins, and the like.

The lubricating oil may be derived from unrefined, refined, re-refined oils, or mixtures thereof. Unrefined oils are obtained directly from a natural source or synthetic source (e.g., coal, shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to unrefined oils, except that refined oils have been treated in one or more purification steps to improve one or more properties. Suitable purification techniques include distillation, hydrotreating, dewaxing, solvent extraction, acid or base extraction, filtration, percolation, and the like, all of which are well-known to those skilled in the art. Re-refined oils are obtained by treating refined oils in processes similar to those used to obtain the refined oils. These re-refined oils are also known as reclaimed or reprocessed oils and often are additionally processed by techniques for removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fischer-Tropsch process. The resulting isomerate product is typically subjected to solvent dewaxing and fractionation to recover various fractions having a specific viscosity range. Wax isomerate is also characterized by possessing very high viscosity indices, generally having a V.I. of at least 130, preferably at least 135 or higher and, following dewaxing, a pour point of about −20° C. or lower.

The lubricating oil used in the practice of the present invention can be selected from any of the base oils in Groups I-V as broadly specified in the American Petroleum Institute (API) Base Oil Interchangeability Guidelines. The five base oil groups are described in Table 1.

TABLE 1

| API Base Oil Category | Sulfur (%) | Saturates (%) | Viscosity Index |
|---|---|---|---|
| Group I | >0.03 and/or | <90 | 80 to 120 |
| Group II | ≦0.03 and | ≧90 | 80 to 120 |
| Group III | ≦0.03 and | ≧90 | ≧120 |
| Group IV | All poly-α-olefins (PAOs) | | |
| Group V | All other not included in Groups I, II, III, or IV | | |

Returning to the additive blend, in one embodiment the composition comprises an additive blend comprising the substituted phosphite and at least one primary antioxidant and one or more additional additives selected from the group consisting of viscosity index improvers, corrosion inhibitors, dispersants, lube oil flow improvers, detergents/rust inhibitors, pour point depressants, antifoamants, antiwear agents, seal swell agents, and friction modifiers. Representative weight percentages of each additive, when present, are based on the total weight of the composition of one embodiment is provided in Table 2.

TABLE 2

| Component | Wt % Range | Preferred Wt % Range |
|---|---|---|
| A) Lubricating Base Stock | Balance | Balance |
| B) Additive Blend | | |
| i. Antioxidants | 0.01-5 | 0.9-3 |
|    a. Substituted Phosphite | 0.01-5 | 0.1-1.5 |
|    b. Secondary Diaryl Amine | 0.01-5 | 0.1-1.5 |
|    c. Substituted Phenol | 0.01-5 | 0.1-1.5 |
| ii. Viscosity Index Improvers | 1-12 | 1-4 |
| iii. Corrosion Inhibitors | 0.01-3 | 0.01-1.5 |
| iv. Dispersants | 0.1-10 | 0.1-5 |
| v. Lube Oil Flow Improvers | 0.01-2 | 0.01-1.5 |
| vi. Detergents/Rust Inhibitors | 0.01-6 | 0.01-3 |
| vii. Pour Point Depressants | 0.01-1.5 | 0.01-0.5 |
| viii. Antifoamants | 0.001-0.1 | 0.001-0.01 |
| ix. Antiwear Agents | 0.001-5 | 0.001-1.5 |

TABLE 2-continued

| Component | Wt % Range | Preferred Wt % Range |
|---|---|---|
| x. Seal Swell Agents | 0.1-8 | 0.1-4 |
| xi. Friction Modifiers | 0.01-3 | 0.01-1.5 |
| xii. Metal Deactivators | 0.001-0.5 | 0.01-0.2 |

These additives may be used alone or in combination. As shown in Table 2, the additive blend of substituted phosphite and at least one primary antioxidant of the present invention can be used in conjunction with other additives typically found in lubricating oils, as well as other antioxidants. It should be understood the various embodiments contemplate including an additive blend that comprises less than all of the components represented in Table 2. For example, an additive blend may comprise a substituted phosphite, secondary diarylamine, corrosion inhibitor, pour point depressant, and friction modifier. Additionally, for example, the additive blend may comprise a substituted phosphite, substituted phenol, viscosity index improver, dispersant, detergents/rust inhibitor, seal swell agent and friction modifier. These examples and other combinations are included within the scope of the present invention as suitable additive blends that be combined with a lubricating base stock or thermoplastic polymers. U.S. Pat. No. 5,498,809 discloses useful lubricating oil composition additives, the disclosure of which is incorporated herein by reference in its entirety.

When other additives are employed in the additive blend, it may be desirable, although not necessary, to prepare an additive blend comprising concentrated solutions or dispersions of the subject antioxidant blends of the present invention, together with one or more of said other additives from Table 2 whereby several additives can be added simultaneously to the base oil to form the lubricating composition. Dissolution of the additive concentrate into the lubricating oil can be facilitated by solvents and by mixing accompanied by mild heating, but this is not essential. The additive blend will typically be formulated to contain the additives in proper amounts to provide the desired concentration in the final formulation when the additive blend is combined with a predetermined amount of lubricant base stock. Thus, the additive blends of the present invention can be added to small amounts of lubricant base stock or other compatible solvents along with other desirable additives to form additive blends containing active ingredients in collective amounts of, typically, from about 2.5 to about 90 wt %, e.g. about 15 to about 75 wt %, or about 25 to about 60 wt %, by weight additives in the appropriate proportions with the remainder being base stock. The final formulations can typically employ about 0.5 to 20 wt % of the additive blend with the remainder being base stock.

Examples of viscosity index (V.I.) improvers include olefin copolymers, dispersant olefin copolymers, ethylene-α-olefin copolymers wherein the α-olefin may be propylene, 1-butene, or 1-pentene, or the hydrides thereof, polyisobutylenes or the hydrides thereof, styrene-diene hydrogenated copolymers, styrene-maleate anhydride copolymers, and polyalkylstyrenes, and the like.

Examples of corrosion inhibitors include amine complexes, benzotriazole-, tolyltriazole-, thidiazole-, and imidazole-based compounds, and the like. The following is an exemplary corrosion inhibitors and is commercially available from King Industries, Inc.: K-Corr™ 100A2.

Examples of dispersants include polyisobutylene succinimides, polyisobutylene succinate esters, Mannich Base ashless dispersants, and the like.

Examples of lube oil flow improvers include dialkyl fumarate-vinyl acetate copolymers and the like.

Examples of detergents include metallic and ashless alkyl phenates, metallic and ashless sulfurized alkyl phenates, metallic and ashless alkyl sulfonates, metallic and ashless alkyl salicylates, metallic and ashless saligenin derivatives, and the like. Examples of rust inhibitors are polyoxyalkylene polyol, benzotriazole derivatives, and the like.

An example of a pour point depressant is polymethacrylate, and the like.

Example of anti-foamants include polysiloxane, silicones such as dimethylsilicone and fluorosilicone, and the like. The following is an exemplary anti-foamant and is commercially available from Munzing/Ultra Additives: Foam Ban™ MS-575.

Examples of anti-wear additives that can be used in combination with the additives of the present invention include organoborates, organophosphites, organophosphates, organic sulfur-containing compounds, sulfurized olefins, sulfurized fatty acid derivatives (esters), chlorinated paraffins, zinc dialkyldithiophosphates, zinc diaryldithiophosphates, dialkyldithiophosphate esters, diaryl dithiophosphate esters, phosphosulfurized hydrocarbons, and the like. The following are exemplary of such additives and are commercially available from The Lubrizol Corporation: Lubrizol 677A, Lubrizol 1095, Lubrizol 1097, Lubrizol 1360, Lubrizol 1395, Lubrizol 5139, and Lubrizol 5604, among others; and from Ciba-Geigy: Irgalube 353.

Examples of seal swell agents include aromatic compounds, sulfur-based compounds, and the like.

Examples of friction modifiers include fatty acid esters and amides, organo molybdenum compounds, molybdenum dialkyldithiocarbamates, molybdenum dialkyl dithiophosphates, molybdenum disulfide, tri-molybdenum cluster dialkyldithiocarbamates, non-sulfur molybdenum compounds and the like. The following are exemplary of molybdenum additives and are commercially available from R. T. Vanderbilt Company, Inc.: Molyvan™ A, Molyvan L, Molyvan 807, Molyvan 856B, Molyvan 822, Molyvan 855, among others. The following are also exemplary of such additives and are commercially available from Asahi Denka Kogyo K.K.: SAKURA-LUBE™ 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, among others. The following are also exemplary of such additives and are commercially available from Akzo Nobel Chemicals GmbH: Ketjen-Ox™ 77M, Ketjen-Ox 77TS, among others. Naugalube MolyFM is also exemplary of such additives and is commercially available from Chemtura Corporation.

Examples of metal deactivators include N,N'-disalicylidene-1,2-propanediamine, benzotriazole and derivatives thereof, and triazole and derivatives thereof. The following are also exemplary of such additives and are commercially available from Ciba-Geigy: Irgamet™ 39. In one embodiment, the additive blend comprises a substituted phosphite, at least one primary antioxidant and is substantially free of metal deactivators, i.e. contains less than 0.05 wt % based on the total weight of the composition of metal deactivators, e.g. less than 0.02 wt % or less than 0.001 wt %.

In another embodiment the substituted phosphite, or an additive blend comprising the substituted phosphite, are particularly useful in thermoplastic polymers, such as polyolefins, polycarbonates, polyesters, polyphenylene ethers and styrenic polymers, due to the extreme temperatures at which thermoplastic polymers are often processed and/or used. In one embodiment, such a composition comprises from about 75 to 99.9 wt % based on the total weight of the composition, e.g. 85 to 99.5 wt % or 90 to 99.1 wt %, of thermoplastic polymers. The composition may also comprise from about 0.1 to 25 wt %, e.g. 0.5 to 15 wt % or 0.9 to 10%, of the substituted phosphite. Optionally, the composition may also comprise from about 0.1 to 25 wt %, e.g. 0.5 to 15 wt % or 0.9 to 10%, of an additive blend comprising a substituted phosphite and at least one primary antioxidant.

Polymers of monoolefins and diolefins, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-co-polymers, LDPE/EVA, LDPE/EAA, LLDPE/EVA, and LLDPE/EAA.

The olefin polymers may be produced by, for example, polymerization of olefins in the presence of Ziegler-Natta catalysts optionally on supports such as, for example, MgCl$_2$, chromium salts and complexes thereof, silica, silica-alumina and the like. The olefin polmers may also be produced utilizing chromium catalysts or single site catalysts, e.g., metallocene catalysts such as, for example, cyclopentadiene complexes of metals such as Ti and Zr. As one skilled in the art would readily appreciate, the polyethylene polymers used herein, e.g., LLDPE, can contain various comonomers such as, for example, 1-butene, 1-hexene and 1-octene comonomers.

Polymers may also include styrenic polymers, such as polystyrene, poly-(p-methylstyrene), poly-(-methylystyrene), copolymers of styrene or -methylstyrene with dienes or acrylic derivatives, such as, for example, styrene/butadiene, styrene/acrylonitrile, styrene/alkyl methacrylate, styrene/maleic anhydride, styrene/maleimide, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene styrene.

Styrenic polymers may additionally or alternatively include graft copolymers of styrene or -methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Nitrile polymers are also useful in polymer compositions of the present invention. These include homopolymers and copolymers of acrylonitrile and its analogs, such as polymethacrylonitrile, polyacrylonitrile, acrylonitrile/-butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo- and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Thus, the thermoplastic resins stabilized by the phosphite compositions of the present invention may optionally contain an additional stabilizer or mixture of stabilizers selected from the group consisting of the phenolic antioxidants, hindered amine stabilizers, the ultraviolet light absorbers, phosphites, phosphonites, alkaline metal salts of fatty acids, the hydrotalcites, metal oxides, epoxydized soybean oils, the hydroxylamines, the tertiary amine oxides, lactones, thermal reaction products of tertiary amine oxides, and the thiosynergists.

Thus, the resulting stabilized polymeric resin compositions optionally also contain various conventional additives, such as the following:

Antioxidants: Antioxidants may comprise alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(-methylcyclohexyl)-4,6dimethylphenol, 2,6-di-octadecyl-4-methylphenol, 2,4,6,-tricyclohexylphenol, 2,6-di-tert-butyl-4-methoxymethylphenol. Alkylated hydroquinones, for example, 2,6di-tert-butyl-4-methoxyphenol, 2,5-di-tert-butylhydroquinone, 2,5-di-tert-amyl-hydroquinone, 2,6 diphenyl-4-octadecyloxyphenol, may also be used as antioxidants.

Antioxidants used may also comprise hydroxylated thiodiphenyl ethers, for example, 2,2'-thio-bis-(6-tert-butyl-4-methylphenol), 2,2'-thio-bis-(4-octylphenol), 4,4'-thio-bis-(6-tertbutyl-3-methylphenol), and 4,4'-thio-bis-(6-tert-butyl-2-methylphenol).

Alkylidene-bisphenols may be used as antioxidants as, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(-methylbenzyl)-4-nonylphenol), 2,2'-methylene-bis-(6-(,-dimethylbenzyl)-4-nonyl-phenol). 2,2'-methylene-bis-(4,6-di-tert-butylphenol), 2,2'-ethylidene-bis-(6-tert-butyl-4-isobutylphenol), 4,4+methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy2-methylphenyl)-3-dodecyl-mercaptobutane, ethyleneglycol-bis-(3,3-bis-(3'-tert-butyl-4'-hydroxyphenyl)-butyrate)-di-(3-tert-butyl-4-hydroxy-5-methylpenyl)-dicyclopentadiene, di-(2-(3'-tert-butyl-2'-hydroxy-5'-methylbenzyl)-6-tert-butyl-4-methylphenyl)terephthalate, and other phenolics, such as monoacrylate esters of bisphenols, such as ethylidiene bis-2,4-di-t-butylphenol monoacrylate ester and esters of 3-5 di butyl hydroxyphenyl propionic acid. The phenolic antioxidants of particular interest are selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)-isocyanurate, thiodiethylene bis (3,5-di-tert-butyl-4-hydroxyhydrocinnamate), 1,3,5-trimethyl-2,4,6-tris(3,5-di-tert-butyl-4-hydroxybenzyl) benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3-tris(2-methyl-4-hydroxy-5-tert-butylphenyl)butane, 1,3,5-tris[2-(3,5-di-tert-butyl-4-hydroxyhydrocinnamoyloxy) ethyl]isocyanurate, 3,5-di-(3,5-di-tert-butyl-4-hydroxybenzyl) mesitol, hexamethylene bis(3,5-di-tert-butyl-4-hyroxyhydrocinnamate), 1-(3,5-di-tert-butyl4-hydroxyanilino)-3,5-di(octylthio)-s-triazine, N,N'-hexamethylene-bis(3,5-di-tert-butyl-4-hydroxyhydrocinnamamide), calcium bis(ethyl3,5-di-tert-butyl-4-hydroxybenzylphosphonate), ethylene bis[3,3-di(3-tert-butyl-4-hydroxyphenyl)butyrate], octyl3,5-di-tert-butyl-4-hydroxybenzylmercaptoacetate, bis(3,5-di-tert-butyl-4-hydroxyhydrocinnamoyl)hydrazide, and N,N'-bis-[2-(3,5-di-tert-butyl-4-hydroxyhydrocinnamoyloxy)ethyl]-oxamide.

Other antioxidants that may be used include benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercaptoacetate, bis-(4-tert-butyl-3-hydroxy-2,6-dimethylbenzyl)dithiol-terephthalate, 1,3,5-tris-(3,5-di-tert-butyl-4,10hydroxybenzyl)isocyanurate, 1,3,5-tris-(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tertbutyl-4-hydroxybenzylphosphonate, and 1,3,5-tris-(3,5-dicyclohexyl-4-hydroxybenzyl)isocyanurate.

Acylaminophenols may be used as antioxidants, for example, 4-hydroxy-lauric acid anilide, 4-hydroxy-stearic acid anilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

Esters of (5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, and dihydroxyethyl oxalic acid diamide may also be used as antioxidants.

Antioxidants may also comprise amides of -(3,5-di-tert-butyl-4hydroxyphenol)-propionic acid, for example, N,N'-di-(3,5-di-tert-butyl-4-hydroxyphenylpropionyl)-hexamethylendiamine, N,N'-di-(3,5-di-tert-butyl-4-hydroxyphenylpropionyl)trimethylenediamine, and N,N'-di (3,5-di-tert-butyl-4-hydroxyphenylpropionyl)-hydrazine.

EXAMPLES

Example 1

Synthesis of
4-oxo-1,3-dioxa-2-phosphanaphthalenes

To a 250 mL Ace flask fitted with temperature probe, addition funnel, stirrer and nitrogen inlet was charged 22.5 g (90 mmoles) of 4-octyl-salicyclic acid and 18.2 g (80 mmoles) of dry triethylamine dissolved on 50 mL dry toluene. Under nitrogen blanketing, to the mixture was added dropwise a solution of 12.3 g (90 mmoles) of $PCl_3$ in 50 mL dry toluene with stirring, while the pot temperature was kept at −5° C. to 0° C. $PCl_3$ addition was complete after 90 min. Stirring continued for an extra 15 min. To this reaction mixture, containing predominantly the 2-chloro-4-oxo-1,3-dioxa-2-phosphanaphthalene intermediate, was added dropwise a solution of 11.7 g (90 mmoles) of iso-octanol and 9.09 g (90 mmoles) of dry triethylamine in 30 mL dry toluene over a period of one hour. During the addition, the pot temperature was kept in the range from −5° C. to 0° C. After the addition was complete, cooling was removed and the pot temperature allowed to rise to room temperature, with stirring. Stirring was continued for an extra hour. A precipitate of triethylamine hydrochloride was then filtered off by suction filtration. The filtrate was stored over night in a refrigerator. The next morning any additional precipitate formed in the toluene solution was filtered off. The resultant filtrate was then evaporated to dryness in vacuo to give 78.5 g of a pale yellow viscous liquid. $^{31}$P-NMR analysis gave a characteristic signal at 125 ppm for the 4-oxo-1,3-dioxa-2-phosphanaphthalene product.

Example 2

A lubricating composition is made by mixing Exxon 100 LP base oil with 0.05 wt % of Irgamet 39, 0.03 wt % of K-Corr 100 A2, and 0.005 wt % of a MS-575 defoamant.

Example 3

To the composition of Example 2, 1.0 wt % of the substituted phosphite from Example 1 is added.

Example 4

Blend of Aminic/Phenolic

To the composition of Example 2, 0.5 wt % of Naugalube 438L (complex mixture of mono-, di-, and tri-nonyl diphenyl amines) and 0.5 wt % of Naugalube 531 (octyl3-[3,5-di(tert-butyl)-4-hydroxyphentl]propanoate) is added.

Example 5

To the composition of Example 2, 0.5 wt % of Naugalube 438L and 0.5 wt % of the substituted phosphite from Example 1 is added.

Example 6

To the composition of Example 2, 0.5 wt % of Naugalube 531 and 0.5 wt % of the substituted phosphite from Example 1 is added.

Example 7

To the composition of Example 2, 0.33 wt % of Naugalube 438L, 0.33 wt % of Naugalube 531 and 0.33 wt % of the substituted phosphite from Example 1 is added.

Comparative Examples A-L

The following comparative examples were prepared from U.S. Ser. No. 11/128,929. Comparative A comprises the composition of Example 2, 0.5 wt % of Naugalube 438L and 0.5 wt % of Weston TPP, a triphenyl phosphite. Comparative B comprises the composition of Example 2, 0.5 wt % of Naugalube 438L and 0.5 wt % of Weston TDP, a triisodecyl phosphite. Comparative C comprises the composition of Example 2, 0.5 wt % of Naugalube 438L and 0.5 wt % of Weston 600, a diisodecyl pentaerythritol diphosphite. Comparative D comprises the composition of Example 2, 0.5 wt % of Naugalube 438L and 0.5 wt % of a dilauryl phosphite. Comparative E comprises the composition of Example 2, 0.5 wt % of Naugalube 531 and 0.5 wt % of Weston TPP. Comparative F comprises the composition of Example 2, 0.5 wt % of Naugalube 531 and 0.5 wt % of Weston TDP. Comparative G comprises the composition of Example 2, 0.5 wt % of Naugalube 531 and 0.5 wt % of Weston 600. Comparative H comprises the composition of Example 2, 0.5 wt % of Naugalube 531 and 0.5 wt % of a dilauryl phosphite. Comparative I comprises the composition of Example 2, 0.33 wt % of Naugalube 438L, 0.33 wt % of Naugalube 531 and 0.33 wt % of Weston TPP. Comparative J comprises the composition of Example 2, 0.33 wt % of Naugalube 438L, 0.33 wt % of Naugalube 531 and 0.33 wt % of Weston TDP. Comparative K comprises the composition of Example 2, 0.33 wt % of Naugalube 438L, 0.33 wt % of Naugalube 531 and 0.33 wt % of Weston 600. Comparative L comprises the composition of Example 2, 0.33 wt % of Naugalube 438L, 0.33 wt % of Naugalube 531 and 0.33 wt % of a dilauryl phosphite.

PDSC Testing and Results

Each of the compositions of Examples 2-6 and Comparative Examples A-L were tested under the pressurized differential scanning calorimeter (PDSC) conditions shown in Table 3. PDSC data in Table 4 are a measure of the oxidation induction time (OIT) of each blend. The PDSC instrument used is a Mettler DSC27HP manufactured by Mettler-Toledo, Inc. The PDSC method employs a steel cell under constant oxygen pressure throughout each run. The instrument has a typical repeatability of ±5.0 minutes with 95 percent confidence for an OIT of 200 minutes. All test formulations were blended for 15 minutes under a nitrogen atmosphere. For every 50 grams of test blend prepared, 40 µL of oil soluble ferric naphthenate (6 weight percent in mineral oil) was added, prior to PDSC testing, to facilitate 50 ppm of iron in oil. At the beginning of a PDSC run, the PDSC steel cell is pressurized with oxygen and heated at a rate of 40° C. per minute to the isothermal temperature listed in the results table. The induction time is measured from the time the sample reaches its isothermal temperature until the enthalpy change is observed. The longer the oxidation induction time, the better the oxidation stability of the oil. Each data point is the average of two runs on a single test blend.

TABLE 3

| Test Parameters | PDSC Test Conditions |
|---|---|
| Temperature | Variable (165° C. or 185° C., see Table 4) |
| O₂ pressure | 500 psi |
| O₂ flow | 100 ml/min |
| Sample size | ~1.5 mg |
| Catalyst | 50 ppm of Fe |
| Sample holder | Open Aluminum Pan |

The advantages and the important features of the present invention for use as lubricant antioxidant are demonstrated in an industrial "R&O" turbine oil formulation. The results are shown in Table 4, where longer times indicates a more stable composition. Unless indicated the values in Table 4 are given in wt %.

TABLE 4

| | | | Phosphites | | | | PDSC | | |
|---|---|---|---|---|---|---|---|---|---|
| Example | A* | B** | Example 1 | Weston TPP | Weston TDP | Weston 600 | Dilauryl phosphite | Expected (Min) | Actual (Min) | (° C.) |
| 2 | | | | | | | | — | 2.8 | 185 |
| 3 | | 1.0 | | | | | | — | 34.0 | 185 |
| 4 | 0.5 | 0.5 | | | | | | 4.6 | 10.8 | 185 |
| 5 | 0.5 | | 0.5 | | | | | 20.2 | 271.6 | 185 |
| Com. A | 0.5 | | | 0.5 | | | | 7.8 | 56.1 | 165 |
| Com. B | 0.5 | | | | 0.5 | | | 9.8 | 65.7 | 165 |
| Com. C | 0.5 | | | | | 0.5 | | 5.2 | 223.1 | 185 |
| Com. D | 0.5 | | | | | | 0.5 | 3.7 | 238.0 | 185 |
| 6 | | 0.5 | 0.5 | | | | | 18.4 | 48.8 | 185 |
| Com. E | | 0.5 | | 0.5 | | | | 6.1 | 19.1 | 165 |
| Com. F | | 0.5 | | | 0.5 | | | 8.1 | 16.4 | 165 |
| Com. G | | 0.5 | | | | 0.5 | | 3.5 | 42.4 | 185 |
| Com. H | | 0.5 | | | | | 0.5 | 1.9 | 42.0 | 185 |
| 7 | 0.33 | 0.33 | 0.33 | | | | | 14.3 | 107.5 | 185 |
| Com. I | 0.33 | 0.33 | | 0.33 | | | | 6.1 | 66.4 | 165 |
| Com. J | 0.33 | 0.33 | | | 0.33 | | | 7.5 | 41.1 | 165 |

TABLE 4-continued

| | | | | Phosphites | | | | PDSC | | |
|---|---|---|---|---|---|---|---|---|---|---|
| Example | A* | B** | Example 1 | Weston TPP | Weston TDP | Weston 600 | Dilauryl phosphite | Expected (Min) | Actual (Min) | (° C.) |
| Com. K | 0.33 | 0.33 | | | | 0.33 | | 4.4 | 85.0 | 185 |
| Com. L | 0.33 | 0.33 | | | | | 0.33 | 3.4 | 118.6 | 185 |

A* is Naugalube 438L
B** is Naugalube 531

The test results given in Table 4 demonstrate that Example 3, which contains 1.0 wt % of the substituted phosphite of the present invention, has superior oxidative stability in the PDSC test, when compared to known aminic antioxidants (1.0 wt % of Naugalube 438L=6.3 min. @185° C.), phenolic antioxidants (1.0 wt % of Naugalube 531=2.8 min. @185° C.), or blends thereof (Example 4).

In addition, the test results given in Table 4 demonstrate antioxidant synergies derived from mixtures of the substituted phosphite of the present invention with the primary antioxidants. The synergistic effects are particularly strong in the PDSC testing for Examples 5-7, when compared to the expected values. Example 5 shows synergistic effects that are better than other known phosphites (Comparative Examples A-D). Example 6 shows synergistic effects that are better than other known phosphites (Comparative Examples E-H). Example 7 shows synergistic effects that are comparable or better than other known phosphites (Comparative Examples I-L). In addition, each of Examples 5-7 are better than blends of aminic and phenolic antioxidants shown in Example 4.

In view of the many changes and modifications that can be made without departing from principles underlying the present invention, reference should be made to the appended claims for an understanding of the scope of the protection to be afforded the invention.

The disclosures of all patents, articles and other materials described herein are hereby incorporated, in their entirety, into this specification by reference. Compositions described as "comprising" a plurality of defined components are to be construed as including compositions formed by admixing the defined plurality of defined components. The principles, preferred embodiments, and modes of operation of the present invention have been described in the foregoing specification. What the Applicants submit is their invention, however, is not to be construed as limited to the particular embodiments disclosed, since the disclosed embodiments are regarded as illustrative rather than limiting. Changes can be made by those skilled in the art without departing from the spirit of the invention.

What is claimed is:

1. A compound of the structure:

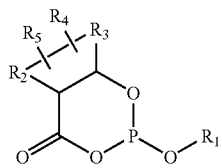

(I)

wherein $R_1$ is $C_4$-$C_{10}$ alkyl;

$R_2$ and $R_3$, together with the carbons to which they are attached, form a $C_5$-$C_{18}$ aryl ring;

$R_4$ is selected from the group consisting of n-butyl, isobutyl, 2,2,3,3-tetramethylbutyl, n-pentyl, 1,3-dimethylpentyl, 3-ethyl-2-methylpentyl, 3-ethyl-3-methylpentyl, 2,3,3-trimethylpentyl, 2,2-dimethylhexyl, 2,3,4-trimethylpentyl, n-hexyl, 1,4-dimethylhexyl, 2,3-dimethylhexyl, 2,5-dimethylhexyl, 2-ethyl-hexyl, 3-ethyl-hexyl, n-heptyl, 2-methylheptyl, 3-methylheptyl, 4-methylheptyl, 1,5-dimethylheptyl, n-octyl, octyl, iso-octyl, nonyl, decyl, $C_4$-$C_{22}$ cycloalkyl, and $C_5$-$C_8$ aryl; and $R_5$ is selected from the group consisting of H, $C_1$-$C_{22}$ alkyl, $C_2$-$C_{22}$ alkenyl, $C_4$-$C_{22}$ cycloalkyl, and $C_5$-$C_8$ aryl.

2. A compound of the structure:

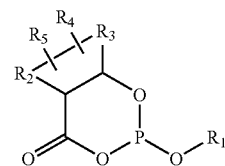

(I)

wherein $R_1$ and $R_4$ are each independently selected from the group consisting of 2-ethyl-hexyl, n-octyl, and iso-octyl;

$R_2$ and $R_3$, together with the carbons to which they are attached, form a $C_5$-$C_{18}$ aryl ring; and $R_5$ is selected from the group consisting of H, $C_1$-$C_{22}$ alkyl, $C_2$-$C_{22}$ alkenyl, $C_4$-$C_{22}$ cycloalkyl, and $C_5$-$C_8$ aryl.

3. A compound of structure (III):

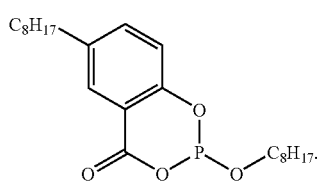

(III)

* * * * *